(12) United States Patent
Bittner

(10) Patent No.: US 11,950,942 B2
(45) Date of Patent: Apr. 9, 2024

(54) SKULL CLAMPING DEVICE FOR FIXING AND ALIGNING A HEAD OF A PATIENT FOR A MEDICAL INTERVENTION

(71) Applicant: Siemens Healthcare GmbH, Erlangen (DE)

(72) Inventor: Maik Bittner, Langensendelbach (DE)

(73) Assignee: SIEMENS HEALTHINEERS AG, Erlangen (DE)

( * ) Notice: Subject to any disclaimer, the term of this patent is extended or adjusted under 35 U.S.C. 154(b) by 888 days.

(21) Appl. No.: 16/745,329

(22) Filed: Jan. 16, 2020

(65) Prior Publication Data
US 2020/0229778 A1 Jul. 23, 2020

(30) Foreign Application Priority Data
Jan. 17, 2019 (DE) .......................... 102019200591.8

(51) Int. Cl.
*A61B 90/14* (2016.01)
*A61B 6/00* (2006.01)
(Continued)

(52) U.S. Cl.
CPC ............ *A61B 6/0421* (2013.01); *A61B 6/485* (2013.01); *A61B 90/14* (2016.02); *A61F 5/3707* (2013.01);
(Continued)

(58) Field of Classification Search
CPC ....... A61B 6/0421; A61B 90/14; A61B 90/10; A61B 5/70; A61B 5/702; A61B 5/704;
(Continued)

(56) References Cited

U.S. PATENT DOCUMENTS

| 5,879,281 A | 3/1999 | Ein-gal |
| 2005/0148808 A1 | 7/2005 | Cameron et al. |

(Continued)

FOREIGN PATENT DOCUMENTS

| CN | 102292038 A | 12/2011 |
| CN | 104983481 A | 10/2015 |

(Continued)

OTHER PUBLICATIONS

German Office Action for German Application No. 10 2019 200 591.8 dated Sep. 13, 2019.

*Primary Examiner* — Victoria Hicks Fisher
(74) *Attorney, Agent, or Firm* — Lempia Summerfield Katz LLC

(57) ABSTRACT

A skull clamping device for fixing and aligning a head of a patient for a medical intervention includes a first ring element and a second ring element arranged concentrically. The second ring element is arranged within the first ring element and is connected hereto by a second axis, about which the second ring element is mounted rotatably within the first ring element. The first ring element is mounted rotatably about a first axis that is orthogonal to the second axis. The skull clamping device also includes a motor-driven drive that drives rotation of the first ring element and/or the second ring element about the respective axis, at least two pins arranged in an innermost ring element, two telescope bars that hold the first ring element and the second ring element, and a control unit for the motor-driven drive.

17 Claims, 4 Drawing Sheets

(51) Int. Cl.
*A61B 6/04* (2006.01)
*A61F 5/37* (2006.01)
*A61G 13/00* (2006.01)
*A61G 13/12* (2006.01)

(52) U.S. Cl.
CPC ........ *A61G 13/0054* (2016.11); *A61G 13/121* (2013.01); *A61G 13/1285* (2013.01)

(58) Field of Classification Search
CPC ............ A61B 2090/101; A61B 5/6814; A61B 17/6433; A61B 17/62; A61B 2018/00321; A61B 6/501; A61F 5/3707; A61F 5/37; A61F 5/05891; A61F 5/05883; A61F 2007/0002; A61F 2007/0008; A61F 2009/0035; A61F 2009/0043; A61G 13/121; A61G 13/1285; A61G 13/128; A61G 13/1205; A61G 13/12; A61G 13/0054; A61G 15/125; A61G 15/12; A61G 13/1295; A61G 13/129; A61G 5/121; A61G 7/072; A61G 7/1084
USPC ........................................................ 128/845
See application file for complete search history.

(56) References Cited

U.S. PATENT DOCUMENTS

| | | |
|---|---|---|
| 2007/0061972 A1 | 3/2007 | Brown et al. |
| 2012/0035612 A1* | 2/2012 | Green .................. A61F 2/4657 606/102 |
| 2015/0265365 A1 | 9/2015 | Andrews et al. |
| 2016/0166324 A1 | 6/2016 | Nyman et al. |
| 2018/0008315 A1 | 1/2018 | Currier |
| 2018/0235824 A1 | 8/2018 | Nordgren et al. |
| 2020/0345572 A1 | 11/2020 | Cooke et al. |

FOREIGN PATENT DOCUMENTS

| | | |
|---|---|---|
| CN | 107106255 A | 8/2017 |
| CN | 109068993 A | 12/2018 |
| CN | 109106454 A | 1/2019 |
| DE | 19718535 A1 | 11/1998 |
| DE | 69631736 T2 | 1/2005 |

* cited by examiner

SKULL CLAMPING DEVICE FOR FIXING AND ALIGNING A HEAD OF A PATIENT FOR A MEDICAL INTERVENTION

This application claims the benefit of DE 10 2019 200 591.8, filed on Jan. 17, 2019, which is hereby incorporated by reference in its entirety.

BACKGROUND

The present embodiments relate to a skull clamping device for fixing and aligning a head of a patient for a medical intervention and a medical imaging system.

Injuries to the cervical spine (e.g., C-spine) are particularly common after car or motorcycle accidents. In this regard, vertebrae may be damaged and fully or partially displaced and exert pressure on the spinal cord as a result. Aside from pain and malposition, in the long term, this may also cause nerve degenerations and lameness and even full paralysis. In order to prevent such aftereffects, the pressure on the spinal cord is to be relieved neurosurgically. In this regard, the affected vertebrae are realigned, and spinal fusion surgery is carried out in order to fix the vertebrae once again.

In order to relieve pressure on the spinal cord neurosurgical and to align the vertebrae, the patient is positioned face down on the operating table. The head is fixed in a Mayfield skull clamp, by which a fixed and secure fixing takes place between two sharp pins. The surgeon then pulls, rotates, and extends the head of the patient, while monitoring under fluoroscopy, until the cervical spine is in the correct position for spinal fusion surgery. In this position, the head is then fixed by the screws of the skull clamp being closed. The surgical intervention is then carried out in this fixed position.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a skull clamping device for fixing and aligning a head of a patient, which eliminates the disadvantages of known devices, is provided.

The present embodiments describe a skull clamping device for fixing and aligning a head of a patient for a medical intervention. The skull clamping device includes at least two ring elements that may be aligned concentrically. A second ring element of the at least two ring elements is mounted rotatably about a second axis within a first ring element of the at least two ring elements. The first, outer ring element is mounted rotatably about a first axis that is orthogonal to the second axis. The skull clamping device also includes at least one motor-driven drive that drives the rotation of at least one of the at least two ring elements about a respective axis, and at least two pins that are arranged in an innermost ring element of the at least two concentric ring elements and are embodied to fix a head of a patient. The skull clamping device includes two telescope bars that hold the ring elements, and a control unit for the motor-driven actuation of the at least one motor-driven drive. A skull clamping device of this type may be used to quickly, easily, and flexibly align the head of a patient for a corresponding intervention in at least two degrees of freedom (e.g., directions of rotation) without the physician having to carry out a time-consuming and laborious manual alignment while illuminating under fluoroscopy. Pressure is therefore taken off the physician and both the physician, and the patient is protected from long and unnecessary x-ray irradiation. The alignment may be carried out in a motor-driven or even automatic manner and minimizes health risks to the patient and physician.

According to one embodiment, the second ring element is the innermost ring element.

According to a further embodiment, the two telescope bars are held on both sides of the first ring element by two brackets so that the first ring element is arranged rotatably about the first axis. An additional degree of freedom or an additional adjustability for the skull clamping device is available on account of the ability of the telescope bars to retract and extend.

According to a further embodiment, the skull clamping device has a third ring element that is alignably arranged concentrically herewith within the second ring element and is connected rotatably with this by a planetary gear. The third direction of rotation is also covered in this way, and the head of the patient may be adjusted in at least three degrees of freedom (e.g., angles of rotation). A planetary gear represents a simple but effective possibility of realizing a third degree of freedom in addition to the two existing degrees of freedom. Four degrees of freedom are possible overall in combination with the adjustable telescope bars.

Alternatively, in a further embodiment, the skull clamping device has a third ring element that is alignably arranged concentrically herewith within the second ring element and is mounted rotatably about a third axis. The third axis is orthogonal to the second axis. This corresponds to a universal mounting and is a further option of easily realizing a third degree of freedom.

For an adjustability in at least three degrees of freedom, the third ring element may be the innermost ring element.

According to a further embodiment, the rotational movements of all ring elements may be motor-driven. In this way, a time-consuming and laborious manual alignment while illuminating under fluoroscopy by the physician is no longer necessary, and the operative intervention may be carried out more quickly and with less risk to the patient and physician. In this way, for an independent adjustment in each of the degrees of freedom, at least one motor-driven drive may be provided for each rotational movement. In one embodiment, a motor-driven drive is also provided to operate the telescope bars.

According to a further embodiment, the control unit is configured to control all available motor-driven drives. In this way, the overall movement of the skull clamping device may be actuated by a single control unit. The control unit may be connected to the device by cable or wirelessly, for example.

According to a further embodiment, the skull clamping device has three or four pins. The three or four pins are arranged in the innermost ring element of the at least two ring elements and are embodied to fix a head of a patient. A significantly more stable fixing of the head of the patient is possible by the one or two additional pins. As a result of this, the risk of injury to the patient by slipping out of the skull clamping device is minimized.

For a particularly stable and anti-slip fixing of the head of the patient, the skull clamping device has a chin guard for additionally holding the head of the patient.

According to a further embodiment, the skull clamping device is configured to be connectable with a patient couch using the telescope bars. In this way, the device is stationary relative to the patient couch. In this way, the risk of injury to the patient is minimized, and a high-quality fluoroscopic imaging by ruling out motion artifacts is provided.

According to a further embodiment, the control unit has a checking unit (e.g., a user interface) for users to input control commands for the motor-driven rotation of the ring elements about corresponding axes. The input rotations are then implemented by the respective drives. The speed of the rotational movement may, for example, be preset or likewise adjusted. The checking unit provides simple operation of the rotations of the ring elements. The checking unit is configured for a particularly simple, rapid, and intuitive operation in that the checking unit has at least three degrees of freedom for operation purposes. A rotational movement about an axis is assigned to each degree of freedom. This may be provided, for example, so that the operating element may be adjusted mechanically even in three degrees of freedom (e.g., in the manner of a joystick).

The present embodiments also include a medical imaging system for recording a three-dimensional (3D) volume image of a patient mounted on a patient couch with a control system, to which a skull clamping device of the present embodiments is assigned.

According to one embodiment, the control system is embodied to determine a proposal for adjusting and/or aligning the ring elements of the skull clamping device from a volume image of a spinal column of a patient with his/her head fixed by the skull clamping device. This may be implemented automatically or semi automatically, for example, after inspection by the physician by the control unit actuating the adjustments of the ring elements and/or the telescope bars, and carrying the adjustments out accordingly.

DETAILED DESCRIPTION

Figure 1:
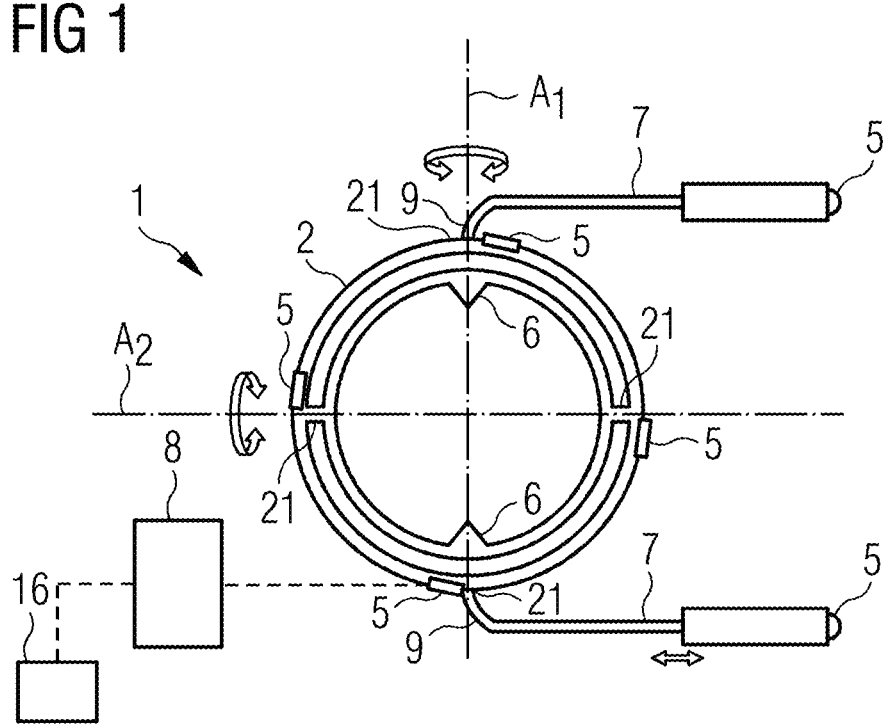
FIG. 1 shows a top view of one embodiment of a skull clamping device with two ring elements.

FIG. 1 shows one embodiment of a skull clamping device 1 with two ring elements, a first ring element 2 and a second ring element 3. Two pins 6 for fixing a head of a patient are arranged in an innermost ring element of the two ring elements, the second ring element 3. The first ring element 2 is arranged rotatably about a first axis $A_1$, where for this purpose, the first ring element 2 is fastened by two bearings 21 to brackets 9, respectively. The two brackets 9, which are arranged in symmetry on both sides of the first ring element 2, are connected to extendible telescope bars 7. The second ring element 3 is arranged within the first ring element 2 and is connected hereto via two bearings 21, so that the second ring element may be rotated about a second axis $A_2$.

Figure 5:
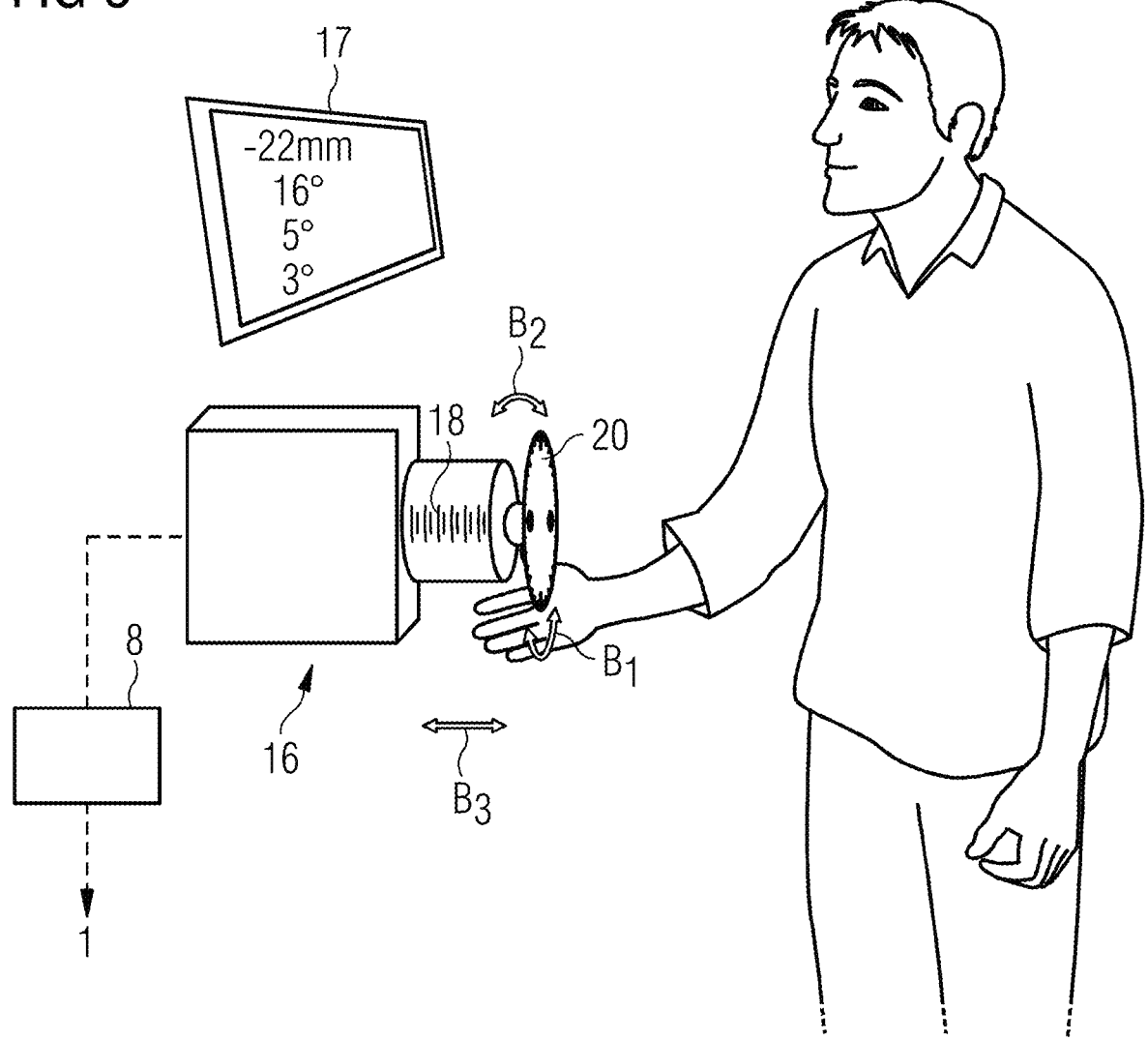
FIG. 5 shows one embodiment of a checking unit for operating a skull clamping device.
Figure 6:
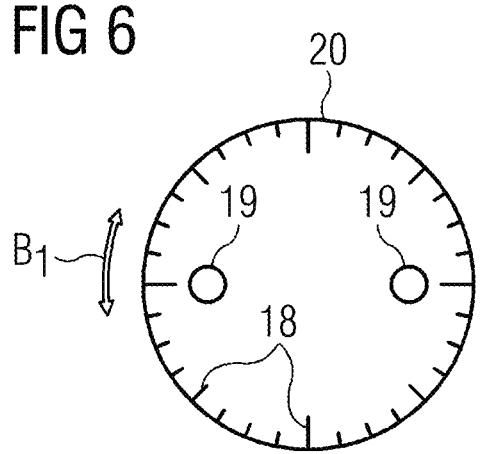
FIG. 6 shows a top view of an exemplary rotating disk of a user interface according to FIG. 5.

A motor-driven drive 5 is assigned to each bearing 21. The motor-driven drive 5 effects a motor-driven rotation of the respective ring element. The first ring element 2 may therefore be rotated about the first axis $A_1$ by two motor-driven drives 5, and the second ring element 3 may be rotated about the second axis $A_2$ likewise by two motor-driven drives 5. The two motor-driven drives 5, which are assigned to an axis, may be actuated in synchrony, for example. Only one motor-driven drive may also be present per axis. Motor-driven drives 5 may also be present for operating the telescope bars 7, as also shown in FIG. 1. A control unit 8 (e.g., a controller) that is embodied to actuate the motor-driven drives 5 is assigned to the skull clamping device 1. The control unit 8 is either connected to the skull clamping device or the motor-driven drives 5 by a connecting line or wirelessly, so that simple and rapid actuation is provided. Provision may also be made for the control unit to be integrated in the skull clamping device 1 (e.g., in the region of the telescope bars 7). The control unit 8 may be operated by a checking unit 16, for example. Details relating to an embodiment of a checking unit 16 are shown in FIGS. 5 and 6.

Figure 2:
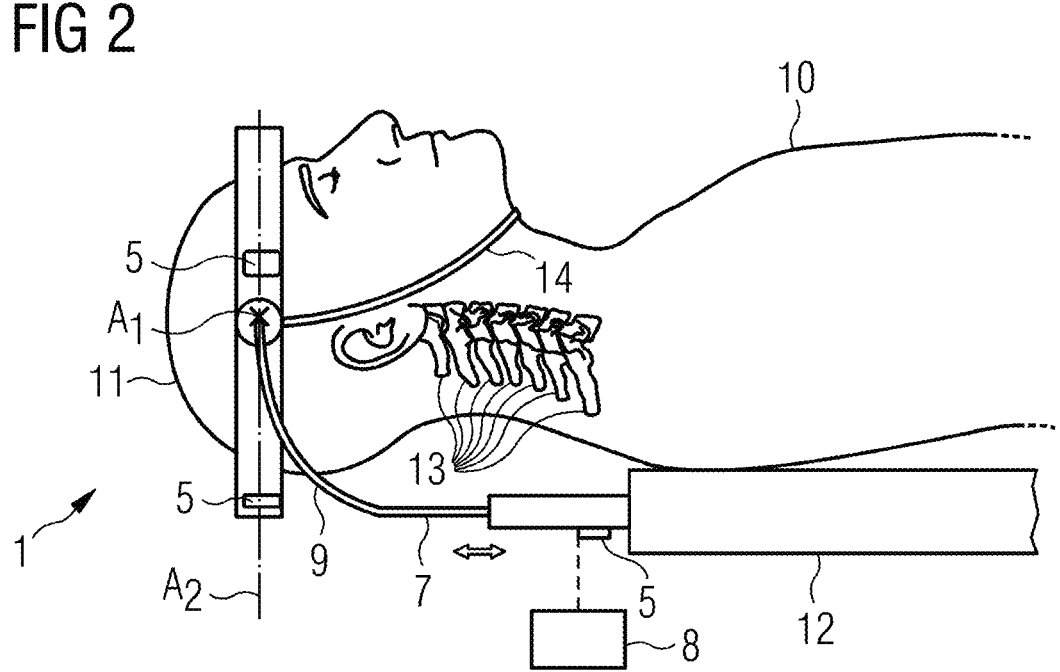
FIG. 2 shows a side view of the skull clamping device according to FIG. 1 with an additional chin guard.

FIG. 2 shows an exemplary skull clamping device 1 from FIG. 1 in a lateral view and rotated by 90° compared with FIG. 1 about the axis $A_1$. The skull clamping device 1 has a chin guard 14 and is connected to a patient couch 12. The head 11 of a patient 10 is clamped into the skull clamping device 1 with the aid of the pins 6, where the chin guard 14 also stabilizes the connection. As already shown in FIG. 1, the first ring element 2 may be rotated about the first axis $A_1$, the second ring element 3 may be rotated about the second axis $A_2$, and the telescope bars 7 may be retracted and extended. The skull clamping device 1 may be used to adjust the position of the head 11 of the patient 10 for an intervention on a cervical vertebra 13 of the patient 10 in a rapid manner that is gentle on the patient and simple for the physician.

Figure 3:
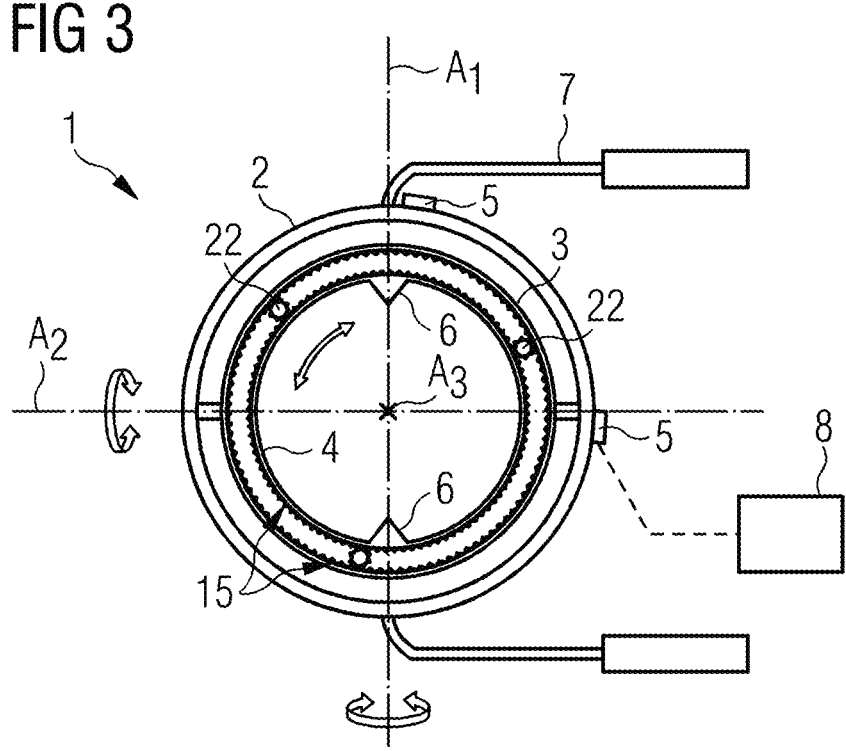
FIG. 3 shows a top view of another embodiment of a skull clamping device with three ring elements and a planetary gear.

A further skull clamping device 1 that has three ring elements is shown in FIG. 3. The first ring element 2 is suspended rotatably about a first axis $A_1$, similarly to in FIGS. 1 and 2 between two telescope bars 7 and two brackets 9. The second ring element 3 is arranged rotatably about the second axis $A_2$ in the inside of the first ring element 2 and concentrically hereto by two further bearings 21. The first axis $A_1$ and the second axis $A_2$ are orthogonal to one another so that the first axis $A_1$ and the second axis $A_2$ cause the head of the patient to tilt in two different directions. A third ring element 4 is arranged inside the second ring element 3 and is connected to the second ring element 3 via a planetary gear so that the third ring element 4 may be rotated about a third axis $A_3$ that is orthogonal to both of the other axes. For greater clarity, only two motor-driven drives 5 are shown; however, at least one motor-driven drive may be available for each axis.

Planetary gears are generally known. The planetary gear shown may, for example, be implemented so that the second ring element 3 (corresponding to the hollow wheel) has teeth on an inner periphery, and the third ring element 4 (correspondent to the sun wheel) likewise has teeth on an outer periphery. A number of likewise toothed small planetary wheels 22 (e.g., three or four planetary wheels 22) are arranged between the two ring elements. The third ring element 4 may be rotated about the third axis $A_3$ by at least one motor-driven drive (not shown here). If the head 11 of the patient 10 is clamped between the pins 6, the head 11 may be positioned in three different rotational directions for an intervention by rotating the three ring elements. The axes may be embodied, for example, so that the rotation about the first axis $A_1$ corresponds to a raising or lowering of the chin of the head, the rotation about the second axis $A_2$ corresponds to a rotation of the head, and the rotation about the third axis $A_3$ corresponds to a manner of shaking the head to the right or left. In addition, the telescope bars 7 may also be retracted and extended, thereby causing a stretching or compression of the spinal column to materialize.

The positioning of the head may be carried out semi automatically or automatically by the motor-driven drives, which may be available for each of the three axes. The drives are actuated by the control unit 8, which may be operated by a user interface 16 (not shown).

In order to avoid interfering artifacts with fluoroscopic illumination of the head, the skull clamping device is manufactured at least partially from an x-ray transparent material. At least the ring elements may be x-ray transparent and are produced from carbon fibers, for example. The motor-driven drives 5 may also have metallic elements. The entire skull clamping device may also be embodied from x-ray transparent material. The arrangement of the telescope bars at the height of the table top allows a largely artifact-free x-ray imaging of the cervical spine.

Figure 4:
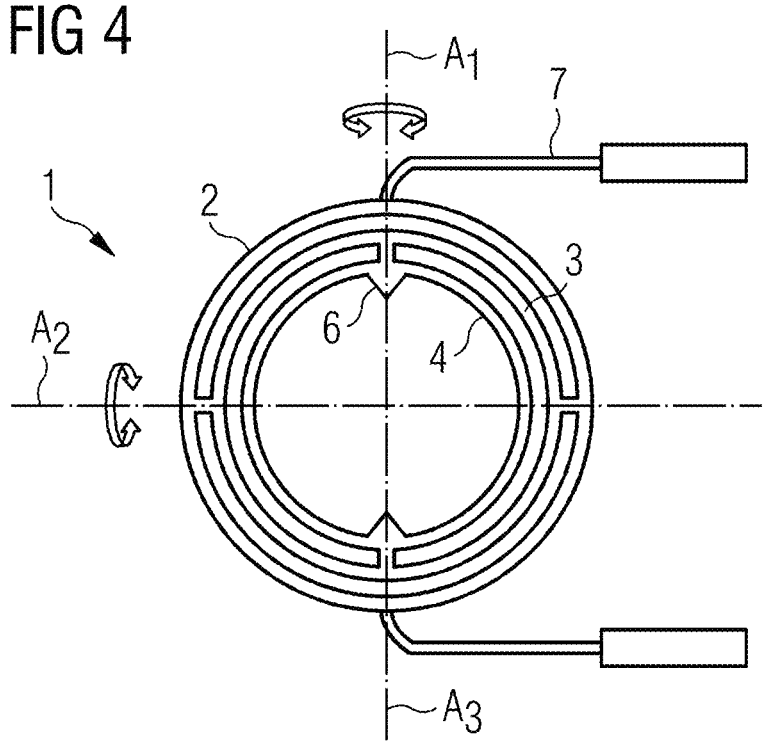
FIG. 4 shows a top view of yet another skull clamping device with three universally mounted ring elements.

FIG. 4 shows a further alternative of a skull clamping device with three ring elements. In FIG. 4, the three ring elements are universally mounted (e.g., the third ring element 4 is arranged alignable concentrically herewith within the second ring element 3 and mounted rotatably about the third axis $A_3$). The third axis $A_3$ is orthogonal to the second axis $A_2$.

The skull clamping devices shown in FIGS. 3 and 4 have four degrees of freedom, three angles of rotation (e.g., rotation of the ring elements about the respective axis) and a longitudinal setting (e.g., deflect telescope bars).

An exemplary checking unit 16 is shown in FIGS. 5 and 6 and is configured for an intuitive actuation of the skull clamping device. The checking unit 16 therefore includes, for example, a rotary disk 20. The user is able to turn the rotary disk 20 in a first movement $B_1$ with thumbs and index fingers using operating holes 19 in order to adjust the skull clamping device. The rotary disk 20 may have a scale 18 to display the gradual adjustment, for example. A second movement $B_2$ corresponds to a tilting of the rotary disk 20, and a third movement $B_3$ corresponds to a pushing/pulling of the rotary disk 20. Operation of the checking unit 16 is then transferred by the control unit 8 to the skull clamping device 1, and the motor-driven drives 5 bring about a corresponding adjustment of the ring elements and/or the telescope bars. In this way, the position of the head of the patient is adjusted quickly but gently and with minimal effort for the user. The precision and sensitivity of the possibilities for adjustment by the checking unit may be smaller than 1 mm and smaller than 1 degree.

Other types of checking units may also be provided for operation by a user in order to actuate the skull clamping device. An input menu on a touch-sensitive monitor may therefore also be easily available, via which it is possible to input angles of rotation for the rotation about the axes $A_1$, $A_2$, and $A_3$ and to input lengths for deflecting the telescope bars.

The user may use a monitor 17 to monitor the settings. The current settings of the skull clamping device may be shown on the monitor 17 (e.g., the three angles of rotation (rotation of the ring elements about the respective axis) and a length setting (deflect telescope bars)).

Provision may be made to regulate the speed of the adjustments or to define threshold values for the angle of rotation, the speed, or the deflection that may not be exceeded. These may either be defined by the user or may already be available as a basic setting. As a result, this may prevent an excessively fast or broad adjustment, so as not to injure the patient. Haptic feedback (e.g., in the form of a vibration) may be available in order to indicate to the user when a threshold value (e.g., an angle of rotation) is reached. Alternatively, optical or acoustic warning signals (e.g., yellow/red light) or displays may also be available in order to point the user to the exceeding of threshold values or signal other warnings. Safety requests or safety cut-outs may also be provided when threshold values are exceeded.

Figure 7:
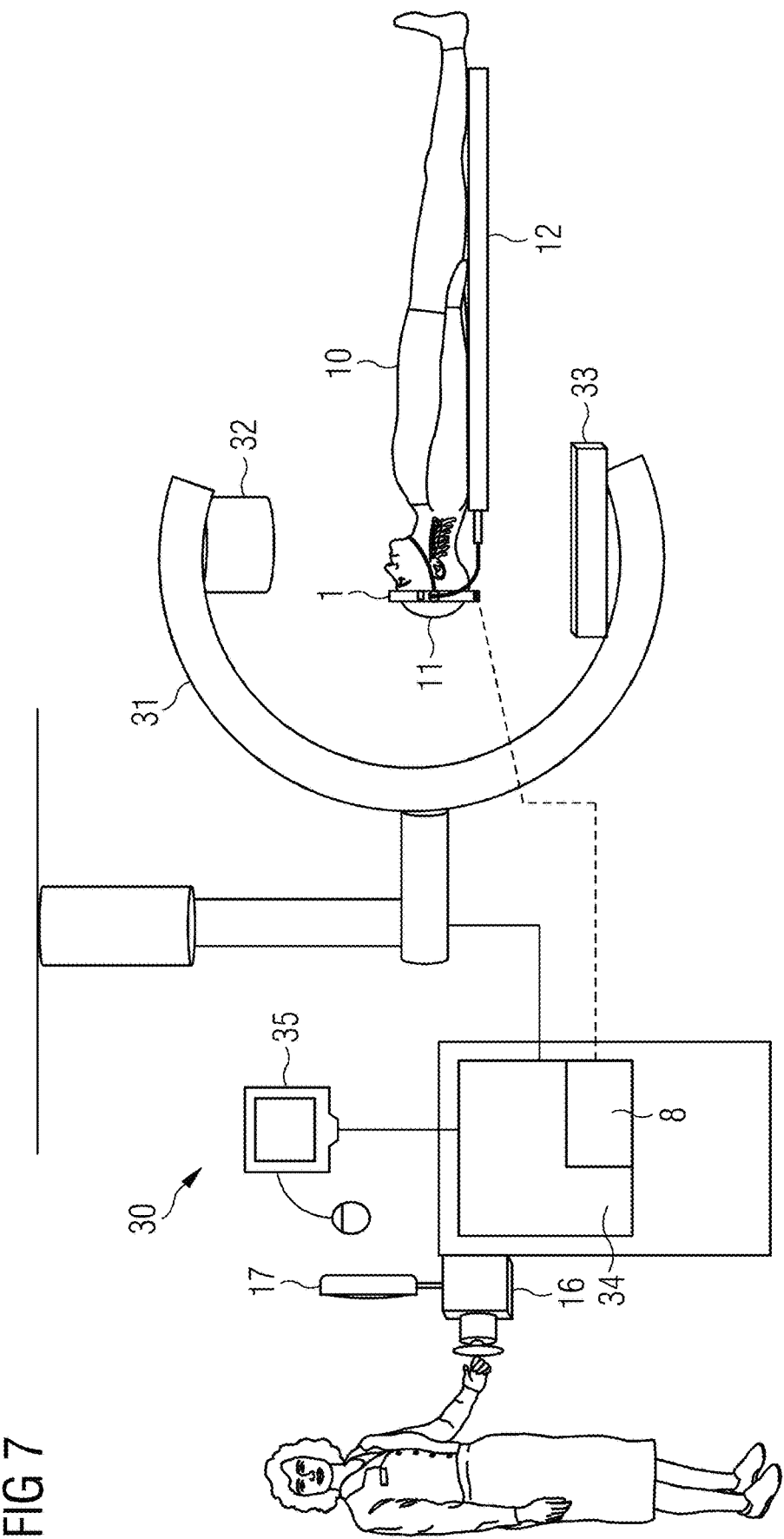
FIG. 7 shows one embodiment of a medical imaging system with an assigned skull clamping device.

FIG. 7 shows one embodiment of a medical imaging system 30 for recording x-ray images of a patient 10 supported on a patient couch. A skull clamping device 1 is assigned to the imaging system 30. The imaging system 30 may be, for example, a C-arm x-ray system with an adjustable C-arm 31 and an x-ray source 32 and an x-ray detector 33 held on the adjustable C-arm 31. The imaging system 30 may be embodied, for example, for a fluoroscopic imaging (e.g., 2D fluoroscopy) and/or for a 3D imaging. The imaging system is actuated by a control system 34. The patient 10 is supported on a patient couch 12, and the head 11 of the patient 10 is fixed by the skull clamping device 1. The patient and the imaging system are located in a hybrid operating room (hybrid OP), for example. The user interface 16 for the user to input control commands may be arranged inside or outside of the operating theater. Provision may be made to arrange the user interface 16 close to the patient couch and in addition behind a lead screen.

A display unit 35 assigned to the imaging system 35 shows, for example, a current x-ray recording of the spinal column and/or of the head of the patient (e.g., in the lateral view (side view)). Various views may be indicated with a biplanar imaging system. The imaging system may alternatively also be formed by a computed tomography system or a magnetic resonance tomography system.

An alignment of a head of a patient for a medical intervention generally takes place such that the cervical spine is extended, and the inclinations are then adjusted so that the bodies of vertebrae move into a suitable position that is required for strengthening the spinal column. This may likewise be carried out with the skull clamping device shown by a lengthening of the telescope bars firstly being actuated and the rotations then being carried out about the axes.

The imaging system shown in FIG. 7 may be used to record a 3D volume image of the cervical spine and/or the head of the patient 10 (e.g., by the C-arm 31 being adjusted in a number of angulations, a plurality of x-ray projections being recorded, and these then being reconstructed to form the volume image). The control system 34 is embodied to determine a proposal for adjusting and/or aligning the ring elements and/or telescope bars of the skull clamping device from the volume image. A calculation unit or software may also be provided herefor. In order to determine such a proposal, further information may also be used (e.g., information about the planned intervention on the cervical spine, which cervical vertebra the planned intervention should involve, further information about the patient, databases relating to similar interventions, etc.).

If a proposal exists, this may be confirmed or rejected by a physician, for example. If the proposal is confirmed or implemented without confirmation, the proposal may then therefore be transferred to the control unit 8 and implemented there automatically or semi automatically by the control unit 8 of the skull clamping device actuating the adjustments of the ring elements and/or the telescope bars and carrying them out accordingly.

The present embodiments have a series of advantages. With skull clamping devices from the prior art, which have no motor-driven drives, the physician is to position the head of the patient manually; this expends effort and time. This usually takes place under fluoroscopy and may last 20 to 30 minutes. In doing so, the physician is to be prudent not to injure the patient. Using the motorized, actuatable and remotely-operable skull clamping device of one or more of the present embodiments, the positioning is significantly simplified, may be carried out more quickly and gently, requires less effort, and is associated with fewer risks to the patient. A dose saving is also to be expected for both the patient and also the physician, since persons are no longer radiated with direct x-ray radiation. Health risks are therefore reduced.

One or more of the present embodiments may be summarized as follows. A skull clamping device is provided for a particularly simple and rapid positioning of a head of a patient for interventions on the cervical spine. The skull clamping device includes at least two ring elements that may be aligned concentrically. The second ring element is mounted rotatably about a second axis within the first ring element, and the first, outer ring element is mounted rotatably about a first axis that is orthogonal to the second axis. At least one motor-driven drive drives the rotation of at least one of the at least two ring elements about a respective axis. At least two pins are arranged in the innermost ring element of the at least two concentric ring elements and are embodied to fix a head of a patient. Two telescope bars hold the ring elements, and a control unit is configured for the motor-driven actuation of the at least one motor-driven drive.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A skull clamping device for fixing and aligning a head of a patient for a medical intervention, the skull clamping device comprising:
    at least two concentrically alignable ring elements, wherein a first ring element of the at least two concentrically alignable ring elements is mounted rotatably about a first axis, and a second ring element of the at least two concentrically alignable ring elements is mounted rotatably about a second axis within the first ring element, the first ring element being outer relative to the second ring element, the first axis being orthogonal to the second axis;
    at least one motor-driven drive configured to drive a rotation of the first ring element about the first axis, a rotation of the second ring element about the second axis, or the rotation of the first ring element about the first axis and the rotation of the second ring element about the second axis;
    at least two holding elements that are arranged in an innermost ring element of the at least two concentrically alignable ring elements, the at least two holding elements being configured to fix the head of the patient, the innermost ring element being the second ring element or a third ring element of the at least two concentrically alignable ring elements; and
    a controller configured for motor-driven actuation of the at least one motor-driven drive.

2. The skull clamping device of claim 1, wherein the at least two holding elements comprise pins.

3. The skull clamping device of claim 1, further comprising two telescoping bars that hold the at least two concentrically alignable ring elements.

4. The skull clamping device of claim 3, wherein the two telescoping bars are held by two brackets on both sides of the first ring element so that the first ring element is arranged rotatably about the first axis.

5. The skull clamping device of claim 1, wherein the at least two concentrically alignable ring elements comprise the third ring element, which is concentrically alignable within the second ring element and is connected rotatably with the second ring element by a planetary gear.

6. The skull clamping device of claim 1, wherein the at least two concentrically alignable ring elements comprise the third ring element, which is concentrically alignable within the second ring element and is mounted rotatably about a third axis, and
    wherein the third axis is orthogonal to the second axis.

7. The skull clamping device of claim 5, wherein the third ring element is the innermost ring element of the at least two concentrically alignable ring elements.

8. The skull clamping device of claim 7, wherein rotational movements of the first ring element, the second ring element, and the third ring element, respectively, are motor-drivable.

9. The skull clamping device of claim 8, wherein the at least one motor-driven drive comprises one or more motor-driven drives for each of the rotational movements.

10. The skull clamping device of claim 3, wherein the at least one motor-driven drive comprises one or more motor-driven drives for operating the two telescoping bars.

11. The skull clamping device of claim 1, wherein the controller is configured to control all motor-driven drives of the at least one motor-driven drive.

12. The skull clamping device of claim 1, wherein the at least two holding elements comprise three or four pins, and
    wherein the three or four pins are arranged in the innermost ring element of the at least two concentrically alignable ring elements and are configured to fix the head of the patient.

13. The skull clamping device of claim 3, wherein the skull clamping device is configured to be connectable to a patient couch with the two telescoping bars.

14. The skull clamping device of claim 1, wherein the controller comprises a checking unit for a user to input control commands for the rotation of the first ring element about the first axis and the rotation of the second ring element about the second axis, which are motor-driven.

15. The skull clamping device of claim 14, wherein the checking unit is configured for three degrees of freedom of movement for operation, and
    wherein a rotational movement about an axis is assigned to each degree of the three degrees of freedom.

16. A medical imaging system for recording a three-dimensional (3D) volume image of a patient supported on a patient couch, the medical imaging system comprising:
- a skull clamping device for fixing and aligning a head of a patient for a medical intervention, the skull clamping device comprising:
  - at least two concentrically alignable ring elements, wherein a first ring element of the at least two concentrically alignable ring elements is mounted rotatably about a first axis, and a second ring element of the at least two concentrically alignable ring elements is mounted rotatably about a second axis within the first ring element, the first ring element being outer relative to the second ring element, the first axis being orthogonal to the second axis;
  - at least one motor-driven drive configured to drive a rotation of the first ring element about the first axis, a rotation of the second ring element about the second axis, or the rotation of the first ring element about the first axis and the rotation of the second ring element about the second axis;
  - at least two holding elements that are arranged in an innermost ring element of the at least two concentrically alignable ring elements, the at least two holding elements being configured to fix the head of the patient, the innermost ring element being the second ring element or a third ring element of the at least two concentrically alignable ring elements; and
  - a controller configured for motor-driven actuation of the at least one motor-driven drive.

17. The medical imaging system of claim 16, wherein the controller is configured to determine a proposal for adjusting, aligning, or adjusting and aligning at least the first ring element and the second ring element of the skull clamping device from a volume image of a spinal column of the patient with the head of the patient fixed by the skull clamping device.

* * * * *